United States Patent [19]

Bennett

[11] Patent Number: Plant 5,670

[45] Date of Patent: Feb. 25, 1986

[54] MINIATURE ROSE PLANT

[76] Inventor: Cecilia L. D. Bennett, 489 Minot Ave., Chula Vista, Calif. 92010

[21] Appl. No.: 525,452

[22] Filed: Aug. 22, 1983

[51] Int. Cl.[4] ..... A01H 5/00

[52] U.S. Cl. ..... Plt./9

[58] Field of Search ..... Plt./9

*Primary Examiner*—Robert E. Bagwill

[57] ABSTRACT

The subject of the present disclosure is a new and distinct variety of miniature rose plant, named 'Think Pink', which is characterized by its blooms of Carmine Rose Pink with softer shades of Carmine Rose on the outer petals and a fragrance similar to 'fresh apples'.

1 Drawing Figure

1

The present invention relates to a new and distinct variety of a hardy, dwarf, bush plant of the miniature class; the variety being primarily characterized as a medium pink.

The variety is further characterized by:

Long stemmed blooms, borne singly or in sprays of 3 to 5 or more, held very erect and well above the foliage.

Has a fragrance very much like 'fresh apples'.

The plant ranges in height from 12 to 18 inches. The canes are sturdy and erect, heavily branched with medium foliage covering. The plant is a moderate to heavy bloomer that does well either outdoors or in the green house.

The plant has good growth habits, well shaped and attractive in appearance, bearing numerous leaflets of average size.

The seed parent was Electron (U.S. Plant Pat. No. 3,226), and the pollen parent was Little Chief (Miniature Rose Plant, deep pink; R. S. Moore; introduced by Sequoia Nursery, 1971).

Subsequent to the origination of the variety, I have successfully reproduced it at TINY PETALS NURSERY located at aforesaid retaining the distinguishing characteristics through succeeding propagations by cuttings.

The descriptive matter which follows pertains to roses grown and color values observed in plants and newly opened blooms in the months of July and August. The plants were grown outdoors in Chula Vista, Calif., and are believed to be accurate standards for this same cultivar in similar conditions of soil and climate elsewhere.

The color photograph illustrates the variety.

Referring now specifically to the new and distinct variety of miniature rose plant named 'Think Pink', the following is a detailed description thereof in outline; all major color plate identifications being by reference to The British Colour Council Horticultural Colour Chart, except where common terms of color definition are employed.

Type: Hardy, dwarf, bushy, green house or outdoor, exhibition quality or garden decorative potted plant.

Class: Miniature.

Variety name: Think Pink

Flowers borne: One to a stem or in sprays of 3 to 5 or more on erect stems with foliage well below the blooms.

Quantity of bloom: Moderate to heavy both outdoors and green house grown.

2

Bud:

*Peduncle.*—Medium to long (averaging 25 to 35 mm); average diameter and sturdy; near Lettuce Green (861/1 to 861/2 page 176) with light to occasionally heavy tinting of bronze.

*Hairs.*—Extremely small and sparse, with none at all on the calyx tube or sepals.

*Calyx.*—Color is near Lettuce Green (861/1 to 861/2 page 176).

*Opening.*—Opens well in all weather.

Bloom:

*Size when fully open.*—Average for a miniature variety (35 to 40 mm).

*Petalage.*—Double — Averaging about 25 to 30 petals, arranged regularly plus petaloids (6 to 10 or more).

*Form.*—Urn-shaped to ovoid as the bloom progresses. The petals remain at first somewhat tightly cupped with the tips and/or margins reflexed outward, becoming at maturity more loosely cupped. Even at the fully opened stage, the petals show little or no rolling under of the margins.

Petals: Fairly thick with good substance with a sheen to the upper surfaces and a matte finish on the under surfaces.

*Shape.*—Outer petals are a very broad obovate form with a slight peak at the apex. The intermediate and inner petals are also obovate shaped, but much narrower; some may even be called broad lanceolate in form. The petaloids are like small lances.

Color: Newly opened flowers from plants grown outdoors (July and August 1983), Chula Vista, Calif.:

*Outside petals.*—Upper surface — Near Carmine Rose (621/3 to 621/2 page 75) with a small area at the base of near Mimosa Yellow (602/1 to 602/2 page 143).

*Under surface.*—The same as the upper surface.

*Intermediate petals.*—Upper surface — Near Carmine Rose (621/2 to 621/1 page 75) with a small area at the base of near Mimosa Yellow (602/1 to 602/2 page 143).

*Under surface.*—The same as the upper surface.

*Inner petals.*—Upper surface — Near Carmine Rose (621/2 to 621/1 page 75) with a small area at the base of near Mimosa Yellow (602 to 602/1 page 143).

*Under surface.*—The same as the upper surface.

*General color effect.*—Newly opened flowers — Rich Carmine Rose with lighter tones on the outer petals. Three days open — slight paling of the inner petals, giving the appearance of one color (Medium Carmine Rose 621/2 page 75) to the entire bloom. Spent petals drop of cleanly.

*Flower longevity.*—(*August* 1983) Plant in pot 4 to 7 days from bud with sepal down to fully opened bloom. Holding at fully open with only slight fading of the inner petals for an additional 3 to 4 days before bloom begins to drop petals. Cut blooms at livingroom temperature 4 to 5 days or longer. No sign of petal margins rolling under as the bloom ages, giving the fully opened flower an very circular symmetry when viewed from the top with a bright red pistil eye.

Reproductive organs:

*Stamens.*—A generous amount arranged uniformly around the pistil.

*Filaments.*—Varying in length; bright yellow.

*Pollen.*—Abundant.

*Pistil.*—Short, abundant and compact; deep red.

*Styles.*—Short; deep red.

*Ovaries.*—All encased in calyx.

*Hips.*—Some.

*Seed.*—Few or none.

*Sepals.*—Permanent; spear-shaped; open as the bloom opens, but does not recurve against the peduncle.

Foliage:

*Leaves.*—Five to seven leaflets on the average; medium size for a miniature rose plant.

*Leaflets.*—Broad ovate-shaped.

*Margin.*—Very serrated with occasional tinting of bronze.

*Color.*—Ranging from near Lettuce Green (861/1 to 861 page 176) to near Scheeles Green (860/2 through 860 page 175) with occasional bronzing of the margins. The upper surfaces have a satiny finish, and the under surfaces have a matte finish of a slightly lighter shade than the upper surfaces.

*Rachis.*—Medium strength; upper surface is grooved with very small hairs over the length of it. Under surface also contains many very small hairs and some small hooked thorns as well.

*Stipules.*—Varying in length from short to medium; average width; tapering auricles angled outward at about 45 degrees.

Growth:

*Habit.*—Dwarf, bushy, much branched; average height for a miniature rose plant.

*Growth.*—Moderate.

*Canes.*—Medium; sturdy; held very erect.

*Main stems.*—Color — Ranging from near Lettuce Green (861/1 to 861 page 176) to near Scheeles Green (860/2 through 860 page 175) with little or no bronzing.

*Thorns.*—Numerous; averaging 35 to 45 per 10 cm on the main stems and branches. Pale yellow or reddish in color with occasional bronzing. Ranging in size from small thorns to large and small prickles. May be straight (most typical on main stems or branches) or slightly hooked downward (most typical on the underside of rachis).

*Branches.*—Color — Same as main stems.

The miniature rose plant and its flowers as herein described may vary in slight detail due to climatic, soil and cultural conditions under which the variety may be grown; the present description being of the variety as grown at Chula Vista, Calif.

The following is claimed:

1. A new and distinct variety of miniature rose plant named 'Think Pink' of hardy, dwarf, bush, much branched habit, substantially as illustrated and described, characterized by its blooms of Carmine Rose Pink with softer shades of Carmine Rose on the outer petals and a fragrance of 'fresh apples', easy to propagate from cuttings, with flowers usually borne singly or in sprays of 3 to 5 or more.

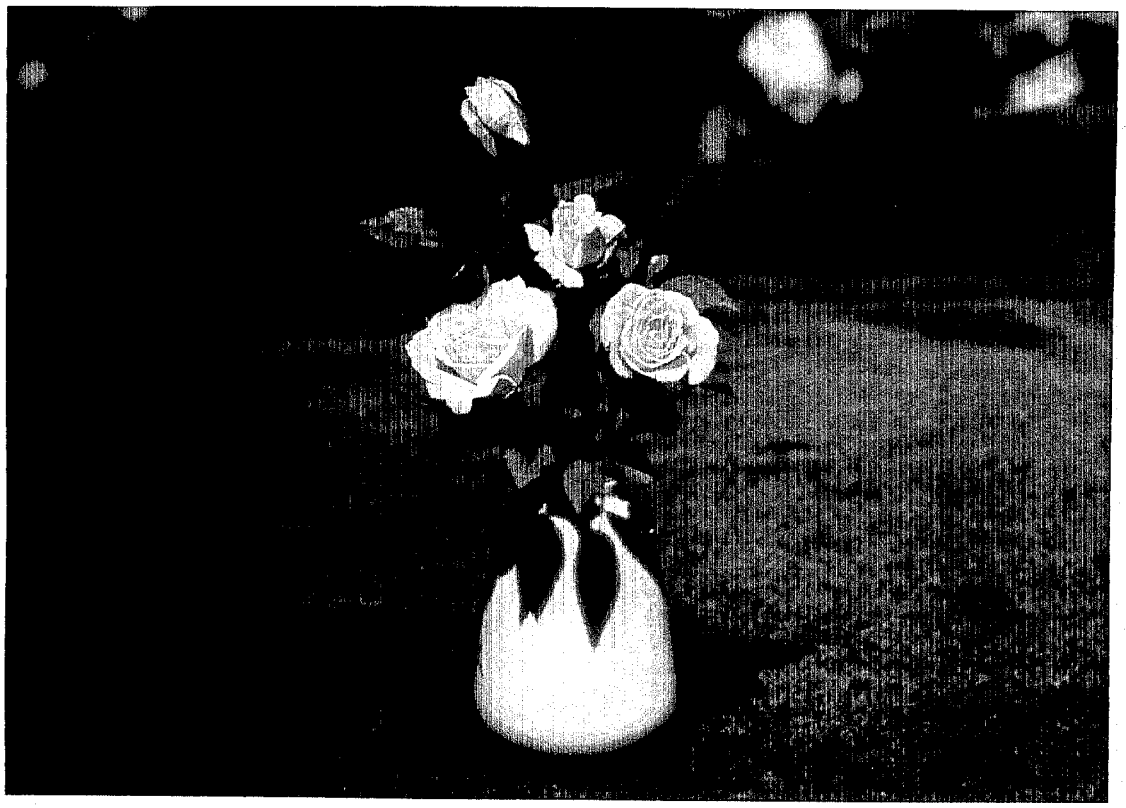

* * * * *